(12) United States Patent
Torres

(10) Patent No.: US 6,610,084 B1
(45) Date of Patent: Aug. 26, 2003

(54) SHAPEABLE PACK FOR COLD THERAPY

(75) Inventor: Ernesto A. Torres, Santa Fe, NM (US)

(73) Assignee: CleanAIR Systems Inc., Santa Fe, NM (US)

(*) Notice: Subject to any disclaimer, the term of this patent is extended or adjusted under 35 U.S.C. 154(b) by 24 days.

(21) Appl. No.: 09/955,011

(22) Filed: Sep. 18, 2001

(51) Int. Cl.$^7$ .................................................. A61F 7/00
(52) U.S. Cl. ........................................ 607/114; 607/108
(58) Field of Search ............................ 607/114, 96, 108

(56) References Cited

U.S. PATENT DOCUMENTS

| 5,129,391 A | | 7/1992 | Brodsky et al. | |
|---|---|---|---|---|
| 5,190,033 A | | 3/1993 | Johnson | |
| 5,409,500 A | | 4/1995 | Dyrek | |
| 5,534,020 A | * | 7/1996 | Cheney et al. | 607/108 |
| 5,545,197 A | * | 8/1996 | Bowen | 607/108 |
| 5,697,961 A | * | 12/1997 | Kiamil | 607/108 |
| 5,723,063 A | * | 3/1998 | Jie | 252/70 |
| 6,051,159 A | | 4/2000 | Hao | |
| 6,099,555 A | | 8/2000 | Sabin | |
| 6,336,935 B1 | * | 1/2002 | Davis et al. | 607/112 |

* cited by examiner

Primary Examiner—Linda C. M. Dvorak
Assistant Examiner—Jocelyn Ram
(74) Attorney, Agent, or Firm—R W Becker & Associates; R W Becker

(57) ABSTRACT

A shapeable, glycerine-free cold pack for providing cold therapy, and a method of producing the same, are provided. The pack comprises a plurality of encapsulated units, wherein a mixture of an NaCl based salt dissolved in water is encapsulated in polyacrylamide. An impermeable enclosure contains the encapsulated units or mini-gels to form the pack, which is pliable over a range of temperatures applicable to cold therapy.

13 Claims, 3 Drawing Sheets

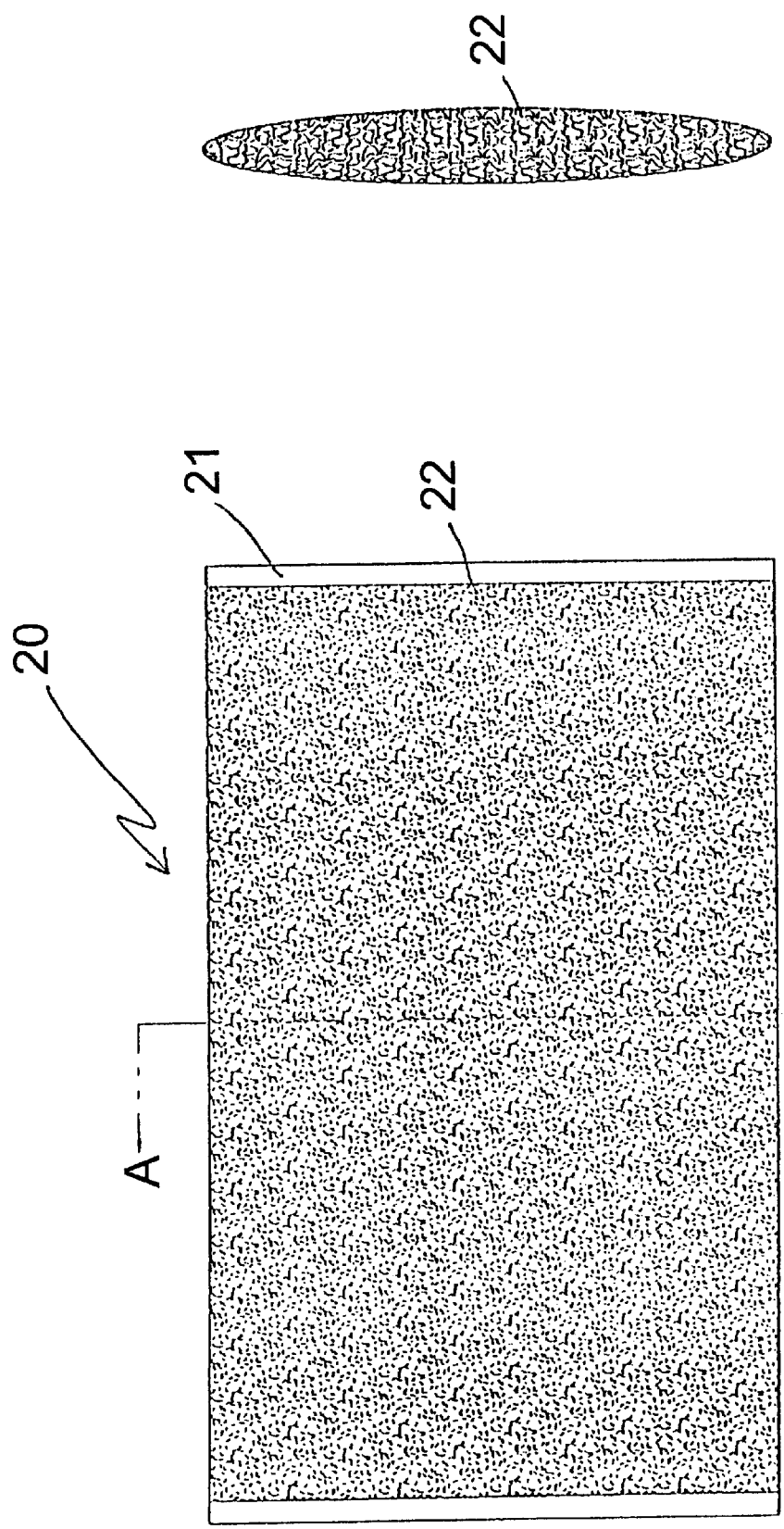

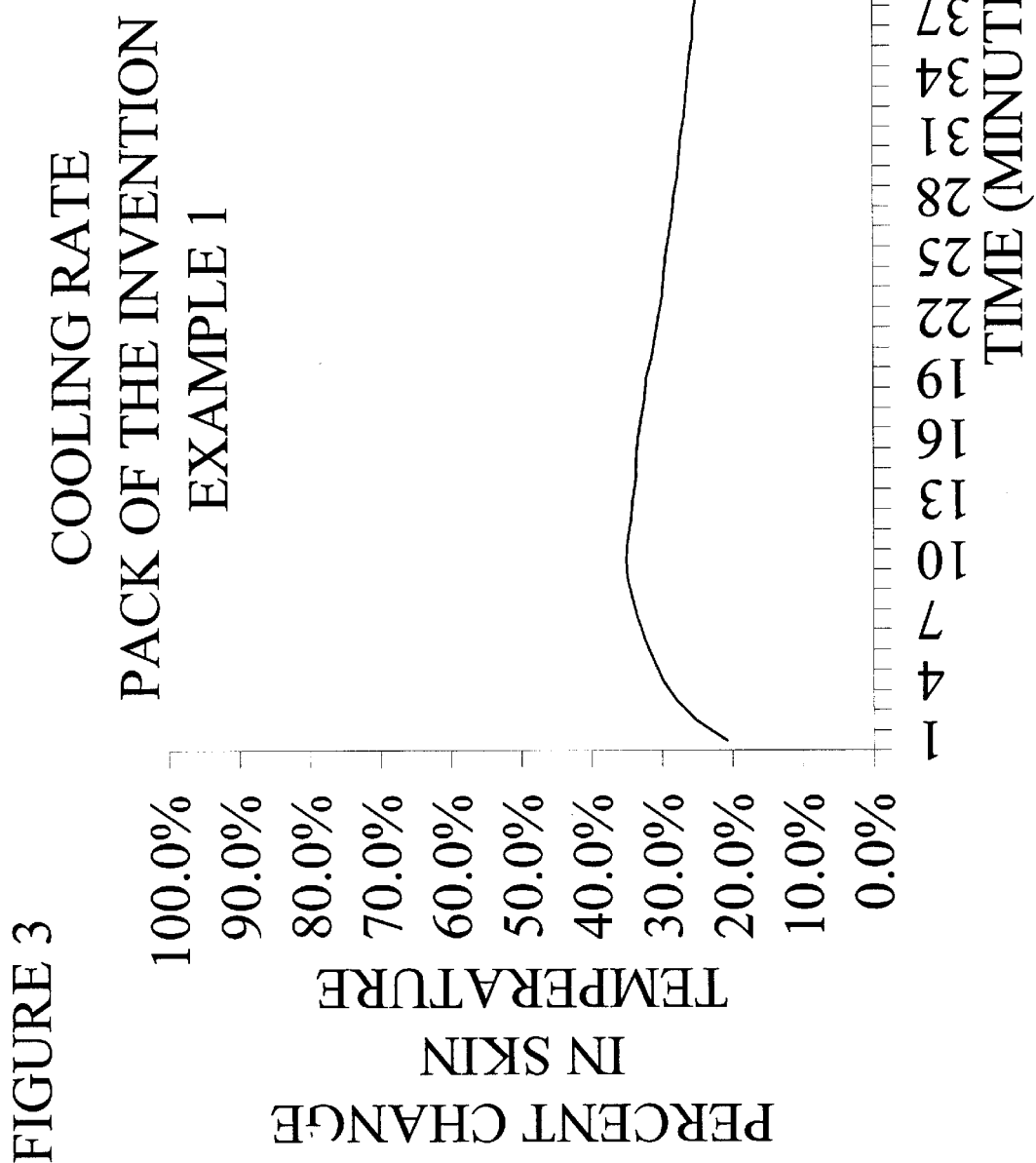

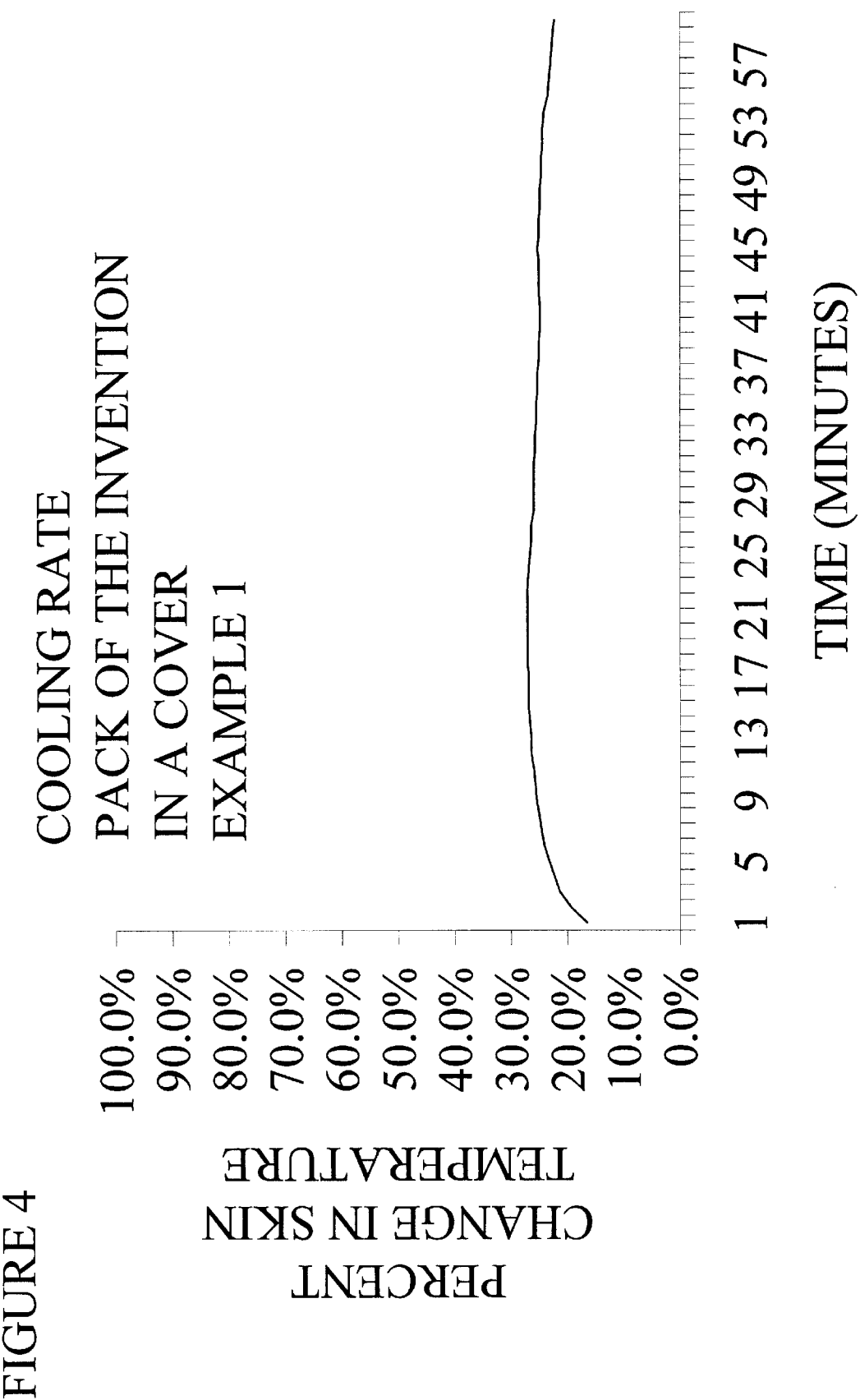

SHAPEABLE PACK FOR COLD THERAPY

FIELD OF THE INVENTION

This invention relates to compositions for use in the preparation of contouring, reusable glycerine-free cold packs that provide cold therapy shapeable to a curved contour of the body, and that have an improved ability to slow down temperature change while maintaining pliancy over a range of temperatures applicable to cold therapy.

BACKGROUND OF THE INVENTION

The use of cold as a therapeutic treatment is as old as the practice of medicine, dating back to Hippocrates. Cold therapy helps reduce or prevent the swelling and pain that accompany musculoskeletal injuries. It can also be used to treat or prevent heat exhaustion, or for general cooling of the body. Cold's therapeutic effects are the result of a reduction in the local metabolic activity of underlying tissues, the slowing of nerve conduction and, by its direct effect on muscle spindle activity, the reduction of muscle spasm.

Ice bags, gel packs, chemical cold packs, immersion and ice massage are the most common methods for delivering cold therapy. Each has advantages and disadvantages:

- the cooling effect of ice bags lasts long, but they do not contour to the body's curves for maximum application;
- cold gel packs can be frozen and refrozen, but require greater caution because they cool the skin fast; and, like ice bags, they do not contour to the body's curves for maximum application;
- chemical cold bags are a good first-aid approach for field or wilderness, but do not produce a great degree of cold;
- immersion of the foot, hand, or elbow in icy water provides complete and concentrated cold exposure, but does not lend itself to other body areas because too much of the uninjured area is exposed to the cold;
- and ice massage is easy to apply and focus, but the cold tends not to penetrate deeply or last as long.

An ideal cold therapy product would, therefore, produce an effective but safe degree of cold over an extended period of time; be very flexible for maximum application to as many areas of the body as possible; and be reusable.

In addressing the demand for cold therapy products, the modern health care industry has significantly focused on gel technology. However, because the technology typically produces a gel that is a semi-solid, single mass, cold gel packs are limited in their ability to conform easily to the injured part of the body for maximum application. The industry has attempted to mitigate this limitation through innovations in packaging that enhances body fit.

A non-industry approach to contouring cold therapy is the common practice of applying a frozen pack of vegetables—usually a pack of frozen peas—to an injured area of the body as a treatment for swelling and pain. Frozen peas, particularly, are mobile and mold into the shape of the body area treated. However, their use is limited because they cannot be frozen and unfrozen repeatedly.

The need for cold packs that address the disadvantages of limited flexibility and application, fast cooling, and limited effectiveness over an extended period of time, as well as the advantage of repeated use, remains current. A variety of approaches have been taken in an attempt to meet this need.

U.S. Pat. No. 5,129,391 to Brodsky, et al, which is incorporated herein in its entirety by reference, discloses a reusable thermal pack that, while frozen, is pliable and contours when placed against injured areas. The pack comprises uniquely shaped packaging, held in place by straps and/or fasteners, and a specially formulated gel that has a greater capacity for cold. The gel is an insoluble, colloidal, homogeneous emulsion that requires several chemicals and other specialized material. In its simplest formulation, it is made of a minimum of one light metal and a plurality of glass beads dispersed in a cellulose material. The process for preparing the gel requires many steps and includes the need for heating and controlled mixing mechanisms. The packaging is varied and complicated. For the gel to contour as effectively as possible, it must be in packs that are specially configured according to the area of the body to be treated. The teaching also discloses steps that must be taken to ensure that the gel does not accumulate in one location within packs of the invention.

U.S. Pat. No. 5,190,033 to Johnson, which is incorporated herein in its entirety by reference, teaches a reusable, cold/hot therapeutic pack that conforms to the natural contours of the body. The pack contains a plurality of thin-walled, hollow capsules containing a temperature storing substance, such as water or gel. The teaching indicates capsules manufactured of non-toxic plastic in a variety of shapes, preferably spherical in shape and one half inch or less in size. The teaching discloses that the ability to conform to the natural contours of the body is delimited by the manner of packaging. The manufacture of different sizes and shapes for application to different parts of the body is required. Because the capsules may be affected by gravity in some applications, special packaging incorporating compartments must be used in these instances. Packs of the invention also require mechanisms for the management of air in order to conform to the body part and provide maximum therapeutic benefit. In addition, manufacturing packs of the invention requires mechanisms for filling the capsules and sealing the filled capsules.

U.S. Pat. No. 5,409,500 to Dyrek, which is incorporated herein in its entirety by reference, teaches a therapeutic cold pack designed to accommodate anatomical surfaces of different sizes, shapes and locations. The pack comprises a plurality of cooling gel compartments, a distribution of predeterminedly anchored straps, and a plurality of mating fasteners on the body of the overlay and at free ends of the straps. The teaching indicates that the delivery of cold therapy to the area of the body being treated is primarily dependent upon the configuration of the pack and, only incidentally, upon the cold providing medium—the cold gel. The design and manufacture of a series of cold packs is required to accommodate not just the areas of the body that contour, but all body areas as well. It is also disclosed that the composition of the cold gel is such that it remains pliant only within temperatures around 0° C., that is, the freezing point of water—again, reinforcing the need for complex, anatomical site-specific design to ensure the cold pack of the invention's claim of versatility, accommodation and effectiveness.

U.S. Pat. No. 6,051,159 to Jie, which is incorporated herein in its entirety by reference, discloses a filling material for cold packs appropriate for laboratory, medical, industrial or home use. The filling is made of varying compositions of water, salt, glycerine and polyacrylamide that are processed in the same manner by dissolving the salt in water and mixing the solution obtained with the glycerine and polyacrylamide until a colloid forms. The resulting filling can then be packaged in a variety of ways according to the intended use. The varying compositions provide a filling material that remains flexible at temperatures no lower than −7° C. There is teaching that indicates that packs of the invention may become too hardened for a particular use and, thus, require softening by kneading with the hands. In addition, the filling alone does not provide maximum flexibility, but requires special packaging.

U.S. Pat. No. 6,099,555 to Sabin, which is incorporated herein in its entirety by reference, discloses a cold pack that utilizes an activatable gelling agent to increase cold persistence, better distribute cold, and more completely utilize its ingredients. To produce cold, the cold pack depends upon the negative heat of solution of a material from one zone dissolving in a liquid from another zone. There is teaching derivable from FIG. 1 of the referenced patent indicating that even though the gelling cold pack may be superior to one that is non-gelling, it still shares a property of cold produced by this method: a constant and significant increase in temperature with each passing minute. That the temperature increase is significant and, very likely, occurs more rapidly than demonstrated is further illustrated by the fact that the test involved only the cold packs' surfaces and the ambient air. No other heat source— for example, an area of the body—is indicated. Yet the teaching states that the cold pack's uses include the cooling of areas of the body for the purpose of treating strained muscles, joints or ligaments, or heat exhaustion. Another limitation is that the cold pack is reusable only insofar as it may be possible to configure it so that it comprises a plurality of first and/or second zones in one pack. Such a pack would then provide the option of generating negative heat of solution more than once. However, there is teaching that discloses that the preferred embodiment is a cold pack disposable after a single use. It is also disclosed that the cold pack is intended for use not only in recreational locations, but in medical facilities and households as well. A cold pack that can operate independently of a refrigerating mechanism may be economical and ecological when used in recreational locations—especially in the case of field or wilderness, for example. But in terms of households and medical facilities, reusable cold packs address both economy and ecology more practicably.

SUMMARY OF THE INVENTION

The present invention provides a material that remedies several of the problems and improves upon many of the advantages presented by cold packs of the prior art. Compositions of the invention produce a smart gel that freezes like packed snow. Cold packs of the invention, therefore, fit flexibly. They contour for maximum application of cold to the injured area of the body. They can be used to treat a broad range of body areas in an uncomplicated manner. Compositions of the invention also exhibit characteristics similar to those of eutectic thermal storage solutions. They slow down temperature change and maintain a generally constant temperature. As a result, cold packs of the invention deliver an even, smooth cold that penetrates and lasts. This type of cold therapy is very beneficial for treating muscle and joint pain, swelling, sprains, and strains. Cold packs of the invention are effective over an extended period of time. They are usable more than once per freezing. Generally, cold is applied 10 to 20 minutes at a time, depending on the body area and comfort. For best results, at least 20 minutes is allowed between uses. This helps control how much an area of the body is cooled and allows the skin to return to normal temperature. A cold pack of the invention can be used at least two times within the hour from when it is first applied. Cold packs of the invention are both economical and ecological.

They can be frozen and unfrozen for repeated use. They are also simple to manufacture and require only a few inexpensive and readily obtainable materials. Compositions of the invention can be cooled to the low temperatures characteristic of freezers in common use and still remain pliant. Temperatures for normal freezing range from as high as −12° C. to as low as −16° C.; for long period storage, normally −18° C. Packs of the invention can be frozen at temperatures as low as −17.56° C. and maintain pliancy.

BRIEF DESCRIPTION OF THE DRAWINGS

FIG. 1 shows a pack of the invention;

FIG. 2 shows a cross-section of a pack of the invention;

FIG. 3 shows the cooling rate of a pack of the invention without a cover; and

FIG. 4 shows the cooling rate of a pack of the invention with a cover.

DETAILED DESCRIPTION OF THE INVENTION

The present invention provides a eutectic glycerine-free material for use in preparing reusable packs to deliver contouring cold therapy to a broad range of body areas. When frozen, the contents of the packs of the invention are snow-like, thus shapeable, and contour easily to fit the area of the body undergoing treatment. The compositions of the invention are simple to manufacture and require only a few inexpensive and readily obtainable materials. Said compositions maintain pliancy at temperatures to as low as −17.56° C. and slow down temperature change. Said compositions thus conform easily to the injured part of the body for maximum application and make available a wide range of temperatures useful for cold therapy. Said compositions also provide steady cooling and increase the number of possible applications per use.

The compositions of the packs of the present invention contain the following materials, in percent by weight of the total composition:

66.67% to 86.41% water;

8.05% to 13.79% of primarily NaCl salt; and 4.59% to 22% polyacrylamide.

The preferred salt is iodized NaCl, for example containing 0.04% dextrose, less than 0.5% calcium silicate, and 0.006 to 0.01% potassium iodide. The preferred water is distilled water. The compositions of the invention are made by dissolving the salt in water, adding the resulting saline solution to the polyacrylamide (in crystal form), and allowing enough time for the polyacrylamide to encapsulate the solution. Packs of the invention are prepared by sealing multiple units of said encapsulated compositions, in such a manner as to allow air to remain present, within an impermeable enclosure that is shapeable over a range of temperatures applicable to cold therapy. Although polyacrylamide is the preferred encapsulating material, other suitable substances could also be used.

EXAMPLES

The following examples describe some of the properties of some particular embodiments of the claimed invention and do not limit the scope of the invention described in the claims.

Example 1

839.5 grams of distilled water were mixed with 113.3 grams of iodized salt until the salt was dissolved. 47.2 grams of polyacrylamide were then added to the saline solution. Sufficient time was allowed for the polyacrylamide crystals to become fully hydrated by the saline solution and form numerous mini-gels. A quantity of mini-gels, sufficient to provide a pack 0.95 cm thick, was then poured into an impermeable bag that was also shapeable over a range of temperatures applicable to cold therapy. The mini-gel filled bag was then sealed in such a manner as to allow air to remain within the resulting pack of the invention.

The resulting pack of the invention was frozen at temperatures as low as −17.56° C. over several days. In the course of freezing, the composition of the invention changed from clear, discrete units of mini-gel to a pliant, crystalline, white snow-like mass. The pliant, snow-like pack was removed from the freezer and conformed to a broad range of body areas, including curved contours such as the knee, ankle, foot, back, elbow and shoulder.

The inventive frozen pack's effect on skin temperature was also tested. The pack was tested both without a cover [FIG. 3] and in a cover, such as a cloth cover [FIG. 4]. Using a thermometer and thermocouple, various temperature readings were taken. Readings included the temperature of the skin before the pack was applied and, during application, continuous skin temperature readings recorded at one-minute intervals over the period of an hour. The pack of the invention—both without a cover and in a cover—exhibited characteristics similar to those of eutectic thermal storage solutions: temperature change was slowed down and a generally constant temperature maintained. The pack of the invention provided steady cooling and made it possible to deliver cold therapy at least twice (20 minutes on, 20 minutes off, 20 minutes on again) before requiring re-freezing.

FIG. 1 shows one exemplary embodiment of an inventive pack 20, which comprises a bag or enclosure 21 that contains a plurality of encapsulated units or mini-gels 22, which can be seen particularly clearly from the cross-sectional view of FIG. 2.

Compositions of the invention are preferably packaged in sealable enclosures or bags made of material that is impermeable to and nonreactive with the compositions, and that remains pliant over a range of temperatures applicable to freezing and to cold therapy. A preferred packaging material consists of metalized polyester and polyethylene copolymer reinforced with vinyl acetate, the combination of which provides an exceptional barrier against gas, moisture, aroma and light, as well as conducts cold more effectively. Other materials would also be suitable. For example, a plain polyethylene bag would be adequate.

Packs of the invention may be made in a variety of shapes and sizes to further conform to different areas of the body when providing cold therapy. Packs may also be applied to the body with or without additional aids such as bands or covers.

Packs of the invention provide both first-aid treatment for musculoskeletal injuries and ongoing relief from associated pain.

Musculoskeletal injuries generally comprise sprains, dislocations, fractures and strains. However, the most common types of musculoskeletal injuries are often the result of overuse of the musculoskeletal system; old injuries that occur again; the normal wear and tear of tendons and joints; or muscle loss associated with aging. Within this context, tendonitis, bursitis and arthritis are also recognized by the orthopedic profession as musculoskeletal impairments.

Cold therapy helps reduce or prevent the swelling and pain that accompany musculoskeletal injuries. The use of cold as a therapeutic treatment is as old as the practice of medicine, dating back to Hippocrates. Modern medicine has since formulated this practice into the combination treatment, R.I.C.E.—rest, ice, compression and elevation.

Cold therapy generally can be used throughout the various stages of healing following an injury. During the first 2 to 3 days after an injury such as joint sprain or muscle strain—the acute stage—cold helps decrease swelling in the area and, therefore, pain by lessening pressure on the nerves. After an injury is 2 to 3 days old—the subacute stage—the body starts trying to heal the injury in a different way. Cold is beneficial during this stage—as well as the chronic stage (i.e., an injury that persists beyond a week)—by reducing the local metabolic activity of underlying tissues, slowing nerve conduction and, by its direct effect on muscle spindle activity, reducing muscle spasm.

Packs of the invention are a practical means for delivering cold therapy to areas of the body affected by musculoskeletal injuries. They produce an effective degree of cold over an extended period of time. They are very flexible for maximum application to as many areas of the body as possible. And they are reusable.

Example 2

A composition comprising a reduced amount of iodized salt and an increased amount of polyacrylamide—the amount of distilled water unchanged—was prepared according to the method stated in Example 1. 839.5 grams of distilled water were mixed with 80.5 grams of iodized salt until the salt was dissolved. 80 grams of polyacrylamide were then added to the saline solution. Sufficient time was allowed for the polyacrylamide to become fully hydrated by the saline solution and form numerous mini-gels.

Example 3

A composition comprising a reduced amount of distilled water and an increased amount of polyacrylamide—the amount of iodized salt unchanged—was prepared according to the method stated in Example 1. 666.7 grams of distilled water were mixed with 113.3 grams of iodized salt until the salt was dissolved. 220 grams of polyacrylamide were then added to the saline solution. Sufficient time was allowed for the polyacrylamide to become fully hydrated by the saline solution and form numerous mini-gels.

Example 4

Packs of the invention were prepared according to the methods stated in Examples 1, 2 and 3 with the exception of one step—freezing. Instead, the resulting packs were refrigerated to lower their temperature for the purpose of delivering cold therapy. Upon removal from the refrigerator, the packs were pliant and conformed to the body wherever applied.

Refrigerating packs of the invention is the preferred method for providing therapeutic cold for treating or preventing heat exhaustion, or for general cooling of the body. Refrigerated packs can be applied very comfortably to areas with little body fat. Such areas tend to be more sensitive to cold than areas with more body fat. For example, cooling the forehead and back of the neck with refrigerated packs may be more beneficial, when treating heat exhaustion or for general cooling, than frozen packs of the invention.

Although in the Examples the polyacrylamide was added to the saline solution, it may be advantageous to add the saline solution to the polyacrylamide.

The instantly claimed invention provides a material that can be cooled to the low temperatures characteristic of freezers in common use, while maintaining the pliancy both necessary and beneficial for the optimum delivery of cold therapy to a broad range of body areas, including its curved contours. Temperatures for normal freezing range from as high as −12° C. to as low as −16° C.; for long period storage, normally −18° C. As stated herein, packs of the invention were frozen at temperatures as low as −17.56° C. and maintained pliancy.

Compositions of the invention are simple to manufacture and require only a few inexpensive and readily obtainable materials. The more useful compositions of the invention necessitate that at least 8.05% by weight be salt.

The present invention is, of course, in no way restricted to the specific disclosure of the specification and drawings, but also encompasses any modifications within the scope of the appended claims.

What I claim is:

1. A shapeable, glycerine-free pack for providing cold therapy to an area of a body for relief of muscle and joint pain, swelling, sprains, and strains, or for treating or preventing heat exhaustion, or for general cooling of the body, comprising:
    a plurality of encapsulated units, wherein a mixture of an NaCl based salt dissolved in water is encapsulated in polyacrylamide, wherein said encapsulated units comprise 66.67 to 86.41% by weight water, 8.05 to 13.79% by weight salt, and 4.59 to 22% by weight polyacrylamide; and
    an enclosure for containing said encapsulated units to form said pack, wherein said pack is pliable over a range of temperatures applicable to cold therapy.

2. A shapeable, glycerine-free pack according to claim 1, wherein said salt is iodized NaCl based salt containing 0.04% dextrose, less than 0.5% calcium silicate, and 0.006 to 0.01% potassium iodide.

3. A shapeable, glycerine-free pack according to claim 1, wherein said water is distilled water.

4. A shapeable, glycerine-free pack according to claim 1, wherein said enclosure is impermeable to and non-reactive with said encapsulated units.

5. A shapeable, glycerine-free pack according to claim 4, wherein said enclosure is made of metalized polyester and polyethylene copolymer reinforced with vinyl acetate.

6. A shapeable, glycerine-free pack according to claim 4, wherein said pack contains air and said enclosure is sealed.

7. A method of providing a shapeable, glycerine-free pack for providing cold therapy to an area of a body, said method including the steps of:
    dissolving an NaCl based salt in water to form a saline solution;
    mixing said saline solution with polyacrylamide to form a plurality of encapsulated units, wherein said encapsulated units comprise 66.67 to 86.41% by weight water, 8.05 to 13.79% by weight salt, and 4.59 to 22% by weight polyacrylamide; and
    disposing said encapsulated units in an enclosure to form said pack, wherein said pack is pliable over a range of temperatures applicable to cold therapy.

8. A method according to claim 7, wherein said salt is iodized NaCl based salt containing 0.04% dextrose, less than 0.5% calcium silicate, and 0.006 to 0.01% potassium iodide.

9. A method according to claim 7, wherein said water is distilled water.

10. A method according to claim 7, wherein said enclosure is impermeable to and non-reactive with said encapsulated units.

11. A method according to claim 10, wherein said enclosure is made of metalized polyester and polyethylene copolymer reinforced with vinyl acetate.

12. A method according to claim 10, wherein said enclosure with said encapsulated units disposed therein, is sealed in such a way that air remains in said pack.

13. A method according to claim 7, which includes the step of freezing or refrigerating a pack produced by the method of claim 7.

* * * * *